US012622585B2

(12) United States Patent
Norman et al.

(10) Patent No.: US 12,622,585 B2
(45) Date of Patent: May 12, 2026

(54) OPHTHALMIC SYSTEM FOR IMAGING THE INTERIOR OF AN EYE

(71) Applicant: PES Innovations, LLC, Fort Worth, TX (US)

(72) Inventors: Alan Andrew Norman, Fort Worth, TX (US); Michael Griffin Hunt, Keller, TX (US); Eric Alan Packwood, Keller, TX (US)

(73) Assignee: PES Innovations, LLC, Fort Worth, TX (US)

( * ) Notice: Subject to any disclaimer, the term of this patent is extended or adjusted under 35 U.S.C. 154(b) by 607 days.

(21) Appl. No.: 17/948,113

(22) Filed: Sep. 19, 2022

(65) Prior Publication Data

US 2024/0090765 A1     Mar. 21, 2024

(51) Int. Cl.
*A61B 3/14* (2006.01)
*H04N 23/56* (2023.01)
*H04N 23/50* (2023.01)

(52) U.S. Cl.
CPC .............. *A61B 3/14* (2013.01); *H04N 23/56* (2023.01); *H04N 23/555* (2023.01)

(58) Field of Classification Search
CPC .... A61B 3/14; A61B 3/10; A61B 3/12; A61B 3/00; A61B 3/113; A61B 3/15; A61B 3/13; A61B 3/16; A61B 3/107; A61B 3/117; A61B 3/02; H04N 23/56; H04N 23/555
See application file for complete search history.

(56) References Cited

U.S. PATENT DOCUMENTS

| | | | |
|---|---|---|---|
| 4,135,791 A | 1/1979 | Govignon | |
| 4,402,325 A * | 9/1983 | Sawa | A61B 3/1241 |
| | | | 600/475 |
| 5,297,554 A * | 3/1994 | Glynn | A61B 5/6821 |
| | | | 600/476 |
| 5,450,144 A * | 9/1995 | Ben Nun | A61F 9/008 |
| | | | 351/219 |
| 12,191,038 B2 | 1/2025 | Norman et al. | |
| 2009/0182311 A1 | 7/2009 | Gertner et al. | |

(Continued)

OTHER PUBLICATIONS

U.S. Appl. No. 17/948,115, entitled, "Method for Analyzing a Retinal Image of an Eye", filed Sep. 19, 2022.

(Continued)

*Primary Examiner* — William R Alexander
*Assistant Examiner* — Matthew Y Lee

(57)     ABSTRACT

In certain embodiments, a system generates image data for an image of the interior of an eye. The system includes a camera apparatus and patient interface. The camera apparatus includes a camera stem, sensor, processor, and communication interface. The camera stem has illuminators that emits light and an objective lens system that receives light. The sensor generates a signal in response to detecting light received by the objective lens system. The processor generates image data from the signal, and the communication interface outputs the image data. The patient interface includes a contact portion and a sleeve. The contact portion is shaped to conform to an anterior eye surface of the eye. The sleeve is shaped to receive the camera stem. The sleeve directs light from the illuminators towards the eye interior, and directs light reflected from the eye interior towards the camera apparatus.

18 Claims, 17 Drawing Sheets

(56)                    References Cited

U.S. PATENT DOCUMENTS

| | | | | |
|---|---|---|---|---|
| 2009/0182312 | A1* | 7/2009 | Gertner | A61F 9/009 |
| | | | | 606/4 |
| 2009/0248442 | A1 | 10/2009 | Pacheco et al. | |
| 2011/0026789 | A1 | 2/2011 | Hsu et al. | |
| 2014/0111628 | A1 | 4/2014 | Yoshino et al. | |
| 2014/0180081 | A1 | 6/2014 | Verdooner | |
| 2014/0267668 | A1* | 9/2014 | Ignatovich | A61B 3/125 |
| | | | | 348/78 |
| 2016/0367134 | A1* | 12/2016 | Su | A61B 3/12 |
| 2017/0281407 | A1* | 10/2017 | Garcia | A61B 3/14 |
| 2019/0014982 | A1 | 1/2019 | Bhuiyan | |
| 2019/0104210 | A1 | 4/2019 | Patton et al. | |
| 2019/0117064 | A1 | 4/2019 | Fletcher et al. | |
| 2019/0142257 | A1 | 5/2019 | Vinther et al. | |
| 2019/0239744 | A1 | 8/2019 | Massie et al. | |
| 2019/0250413 | A1 | 8/2019 | Martin | |
| 2020/0116897 | A1 | 4/2020 | Schadlu et al. | |
| 2020/0281465 | A1 | 9/2020 | Myung et al. | |
| 2021/0019884 | A1 | 1/2021 | Kawai et al. | |
| 2021/0279874 | A1 | 9/2021 | Boyd et al. | |
| 2021/0315455 | A1 | 10/2021 | DeLong et al. | |
| 2022/0000363 | A1 | 1/2022 | Ralston | |
| 2022/0183553 | A1 | 6/2022 | Wang et al. | |
| 2022/0183888 | A1* | 6/2022 | Abraham | A61F 9/00838 |
| 2022/0280028 | A1 | 9/2022 | Moretti et al. | |

OTHER PUBLICATIONS

International Search Report and Written Opinion, by the ISA/US, mailed Jan. 12, 2024, re International Application No. PCT/US2023/032443.

International Search Report and Written Opinion, by the ISA/US, mailed Mar. 1, 2024, re International Application No. PCT/US2023/032440.

Notice of Allowance, dated Oct. 1, 2024, by the USPTO, re U.S. Appl. No. 17/948, 115.

Office Action, dated Jul. 17, 2024, by the USPTO, re U.S. Appl. No. 17/948,115.

Peachpit, "Exploring Frames, Clips, and Sequences in Adobe Premiere Pro CS5" https://www.peachpit.com/articles/articles.aspx?p=1661113&seqNum=2, 2010 (Year: 2010).

* cited by examiner

PATIENT
INTERFACE
20

SLEEVE
26

ANTERIOR
SURFACE
36

LENS
28

α

38
POSTERIOR
SURFACE

24
CONTACT
PORTION

PATIENT
INTERFACE
20

SLEEVE
26

ANTERIOR
SURFACE
36

LENS
28

24
CONTACT
PORTION

38
POSTERIOR
SURFACE

CONTACT
PORTION
24

PATIENT
INTERFACE
20

LENS
28

ANTERIOR
SURFACE
36

38
POSTERIOR
SURFACE

PATIENT
INTERFACE
20

CONTACT
PORTION
24

RIDGE
35

POSTERIOR
SURFACE
38

36
ANTERIOR
SURFACE

PATIENT
INTERFACE
20

SLEEVE
26

LENS
28

RECEPTACLE
33

40
CUFF

24
CONTACT
PORTION

PATIENT
INTERFACE
20

LENS
28

CUFF
40

RECEPTACLE
33

24
CONTACT
PORTION

END
42

IMAGING
SUBSYSTEM
48

CAMERA
STEM
30

HANDLE
44

ILLUMINATOR
FIBERS
50

LIGHT
SOURCE
54

52
PROCESSOR

22
CAMERA
APPARATUS

56
CONTROLS

34
COMMUNICATION IF

CAMERA STEM
30

END
42

46
ILLUMINATORS

48
IMAGING SUBSYSTEM

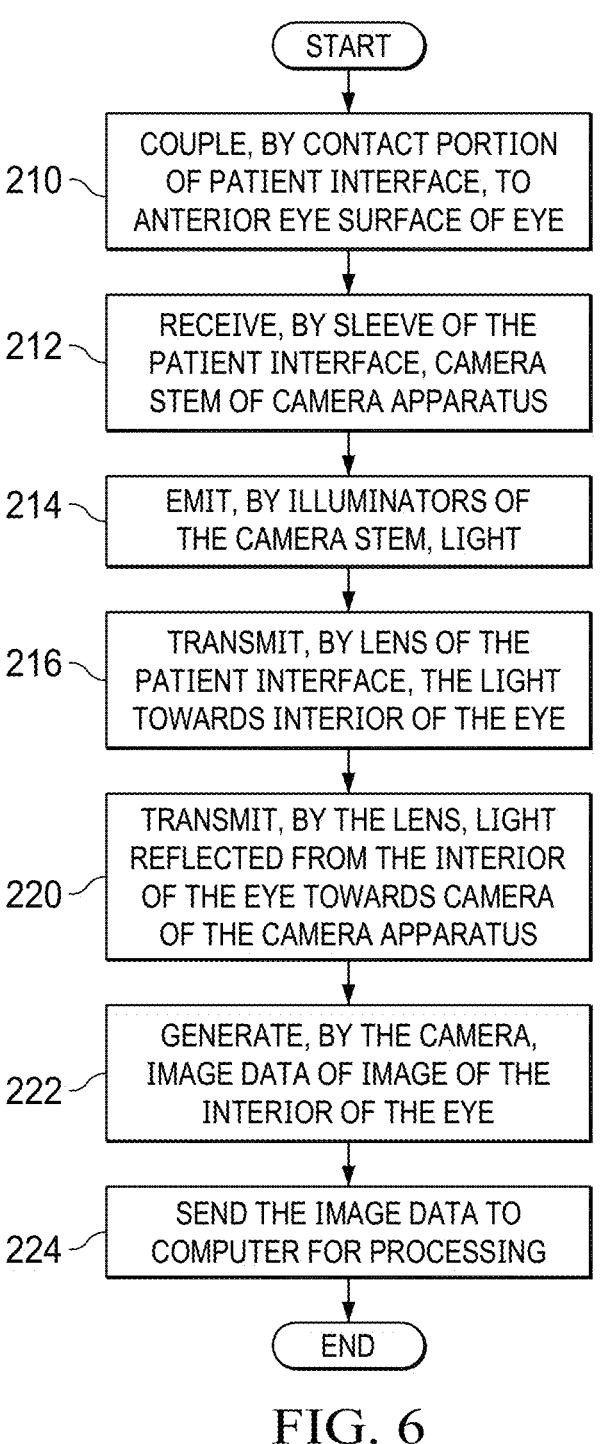

START

210 — COUPLE, BY CONTACT PORTION OF PATIENT INTERFACE, TO ANTERIOR EYE SURFACE OF EYE

212 — RECEIVE, BY SLEEVE OF THE PATIENT INTERFACE, CAMERA STEM OF CAMERA APPARATUS

214 — EMIT, BY ILLUMINATORS OF THE CAMERA STEM, LIGHT

216 — TRANSMIT, BY LENS OF THE PATIENT INTERFACE, THE LIGHT TOWARDS INTERIOR OF THE EYE

220 — TRANSMIT, BY THE LENS, LIGHT REFLECTED FROM THE INTERIOR OF THE EYE TOWARDS CAMERA OF THE CAMERA APPARATUS

222 — GENERATE, BY THE CAMERA, IMAGE DATA OF IMAGE OF THE INTERIOR OF THE EYE

224 — SEND THE IMAGE DATA TO COMPUTER FOR PROCESSING

END

FIG. 6

OPHTHALMIC SYSTEM FOR IMAGING THE INTERIOR OF AN EYE

TECHNICAL FIELD

The present disclosure relates generally to ophthalmic imaging systems, and more particularly to an ophthalmic system for imaging the interior of an eye.

BACKGROUND

Certain ophthalmic diseases can be diagnosed by examining the retina. For example, the retina of a prematurely born baby can be examined to detect retinopathy of prematurity (ROP). ROP is characterized by the disorganized growth of retinal blood vessels, which can result in scarring, retinal detachment, or even blindness.

To examine the retina, an image, e.g., a photograph or video, of the retina may be recorded. In some cases, the image can be sent to a location away from the patient to allow for remote diagnosis of the disease. However, taking an image of the retina may be uncomfortable or even scary for the patient, especially for a baby.

BRIEF SUMMARY

In certain embodiments, a system generates image data for an image of the interior of an eye. The system includes a camera apparatus and patient interface. The camera apparatus includes a camera stem, sensor, processor, and communication interface. The camera stem has a distal end comprising a set of one or more illuminators and an objective lens system. An illuminator emits light, and the objective lens system receives light. The sensor generates a signal in response to detecting light received by the objective lens system. The processor generates the image data from the signal, and the communication interface outputs the image data. The patient interface includes a contact portion and a sleeve. The contact portion has an anterior interface surface and a posterior interface surface, where the posterior interface surface is shaped to conform to the anterior eye surface of the eye. The sleeve is disposed outwardly from the anterior interface surface and shaped to receive the camera stem. The sleeve directs light from the set of illuminators towards the interior of the eye, and directs light reflected from the interior of the eye towards the objective lens system of the camera apparatus, which generates the image data for the image of the interior of the eye.

Embodiments may include none, one, some, or all of the following features:

The posterior end of the sleeve has a ball shape. The anterior interface surface of the contact portion forms a socket shaped to receive the ball-shaped posterior end of the sleeve. The contact portion may have a circular ridge disposed within the socket, the circular ridge circumscribing the opening.

A central portion of the contact portion forms an opening between the anterior interface surface and the posterior interface surface.

A lens is disposed within a central portion of the contact portion. The lens transmits light from the set of illuminators towards the interior of the eye, and transmits light reflected from the interior of the eye towards the objective lens system of the camera apparatus. The lens may be a wide-angle lens with an angle of view in a range of 64 to 84 degrees or an ultrawide-angle lens with an angle of view in a range of 84 to 180 degrees.

The contact portion has a cuff disposed outwardly from the anterior interface surface. The cuff forms a receptacle shaped to receive a depressor for depressing the peripheral retina.

The camera apparatus further includes a handle coupled to the camera stem. The handle has a handle axis, and the camera stem has a stem axis. The stem axis may be at an angle in the range of 0 to 45 degrees relative to the handle axis. The handle may have one or more user controllers. A user controller receives a user instruction to perform an action, and provides the instruction to the processor to perform the action.

The communication interface has an interface for a wired communication link.

The communication interface has an interface for a wireless communication link.

In certain embodiments, a method for generating image data for an image of the interior of an eye includes conforming, by a posterior interface surface of a contact portion of a patient interface, to the anterior eye surface of the eye. A camera stem of a camera apparatus is received by a sleeve of the patient interface. The sleeve is disposed outwardly from an anterior interface surface of the contact portion. The camera stem includes a set of one or more illuminators that emit light and an objective lens system that receives light. Light is emitted by the set of illuminators. Light from the set of illuminators is directed by the sleeve towards the interior of the eye. Light reflected from the interior of the eye is directed by the sleeve towards the objective lens system of the camera apparatus. A signal is generated by a sensor of the camera apparatus in response to detecting light received by the objective lens system. Image data for an image of the interior of the eye is generated by a processor of the camera apparatus from the signal. The image data is output by a communication interface of the camera apparatus.

Embodiments may include none, one, some, or all of the following features:

The posterior end of the sleeve has a ball shape. The anterior interface surface of the contact portion forms a socket shaped to receive the ball-shaped posterior end of the sleeve. The contact portion may have a circular ridge disposed within the socket, the circular ridge circumscribing the opening.

A central portion of the contact portion forms an opening between the anterior interface surface and the posterior interface surface.

A lens is disposed within a central portion of the contact portion. The method further includes: transmitting, by the lens, light from the set of illuminators towards the interior of the eye; and transmitting, by the lens, light reflected from the interior of the eye towards the objective lens system of the camera apparatus.

The contact portion has a cuff disposed outwardly from the anterior interface surface, where the cuff forms a receptacle. The method further includes receiving, by the receptable, a depressor for depressing the peripheral retina.

The camera apparatus further includes a handle coupled to the camera stem, where the handle has one or more user controllers. The method further includes: receiving, by a user controller, a user instruction to perform an action; and providing the instruction to the processor to perform the action.

In certain embodiments, a method for analyzing a retinal image of the retina of an eye for retinal disease includes displaying, at a computer, a graphical user interface (GUI) comprising options. Each option represents an action that facilitates analysis of the retinal image. Image data of the retinal image is received at the computer. The retinal image, which may have one or more frames, is displayed at the computer according to the image data. A selection of an option to facilitate analysis of the retinal image is received at the computer. The action represented by the option is performed, by the computer, in response to the selection to facilitate analysis of the retinal image.

Embodiments may include none, one, some, or all of the following features:

The computer may be a smart phone, tablet computer, laptop computer, or desktop computer.

The options include one or more patient data options designed to gather patient data, such as birth weight, age at birth, or gestational age of the patient. The patient data option may represent an action to receive the patient data entered into a patient data field of the GUI or an action to retrieve a stored patient record comprising the patient data.

The options include one or more image viewing options designed to zoom, focus, or magnify at least a portion of the retinal image.

The options include one or more image analysis options designed to analyze the retinal image for retinal disease. An image analysis option may represent an action to check an image quality of the retinal image or an action to display an overlay onto the retinal image, where the overlay indicates zones of the retina in the retinal image.

The options include one or more image editing options designed to modify the retinal image. An image editing option may represent an action to: select a frame from a video of the retinal image and save the selected frame as a photograph; select frames from a video of the retinal image and save the selected frames as a new video; select one or more frames from a video of the retinal image and remove the selected frames from the video; or receive a markup instruction for placing a marking on the retinal image and place the marking on the retinal image according to the markup instruction.

In certain embodiments, a method for analyzing a retinal image of the retina of an eye for retinal disease includes conforming, by a posterior interface surface of a contact portion of a patient interface, to the anterior eye surface of the eye. A camera stem of a camera apparatus is received by a sleeve of the patient interface, which is disposed outwardly from an anterior interface surface of the contact portion. Light from the camera stem is directed by the sleeve towards the interior of the eye. Light reflected from the interior of the eye is directed by the sleeve towards the camera apparatus. Image data for the retinal image is generated by the camera apparatus in response to detecting the reflected light. The image data is output by a communication interface of the camera apparatus to a computer. A graphical user interface (GUI) comprising options is displayed at the computer. Each option represents an action that facilitates analysis of the retinal image. The retinal image, which may have one or more frames, is displayed at the computer according to the image data. A selection of an option to facilitate analysis of the retinal image is received at the computer. The action represented by the option is performed by the computer in response to the selection to facilitate analysis of the retinal image.

Embodiments may include none, one, some, or all of the following features:

The options include one or more patient data options designed to gather patient data such as birth weight, age at birth, and gestational age of the patient.

The options include one or more image viewing options designed to zoom, focus, and magnify at least a portion of the retinal image.

The options include one or more image analysis options designed to analyze the retinal image for retinal disease. An image analysis option may represent an action to display an overlay onto the retinal image, where the overlay indicates zones of the retina in the retinal image.

The options include one or more image editing options designed to modify the retinal image.

BRIEF DESCRIPTION OF THE DRAWINGS

FIG. 6 illustrates an example of a method for capturing an image of the interior of a patient eye that may be performed by the medical device of FIG. 1, according to certain embodiments.

DESCRIPTION OF EXAMPLE EMBODIMENTS

Figure 1:
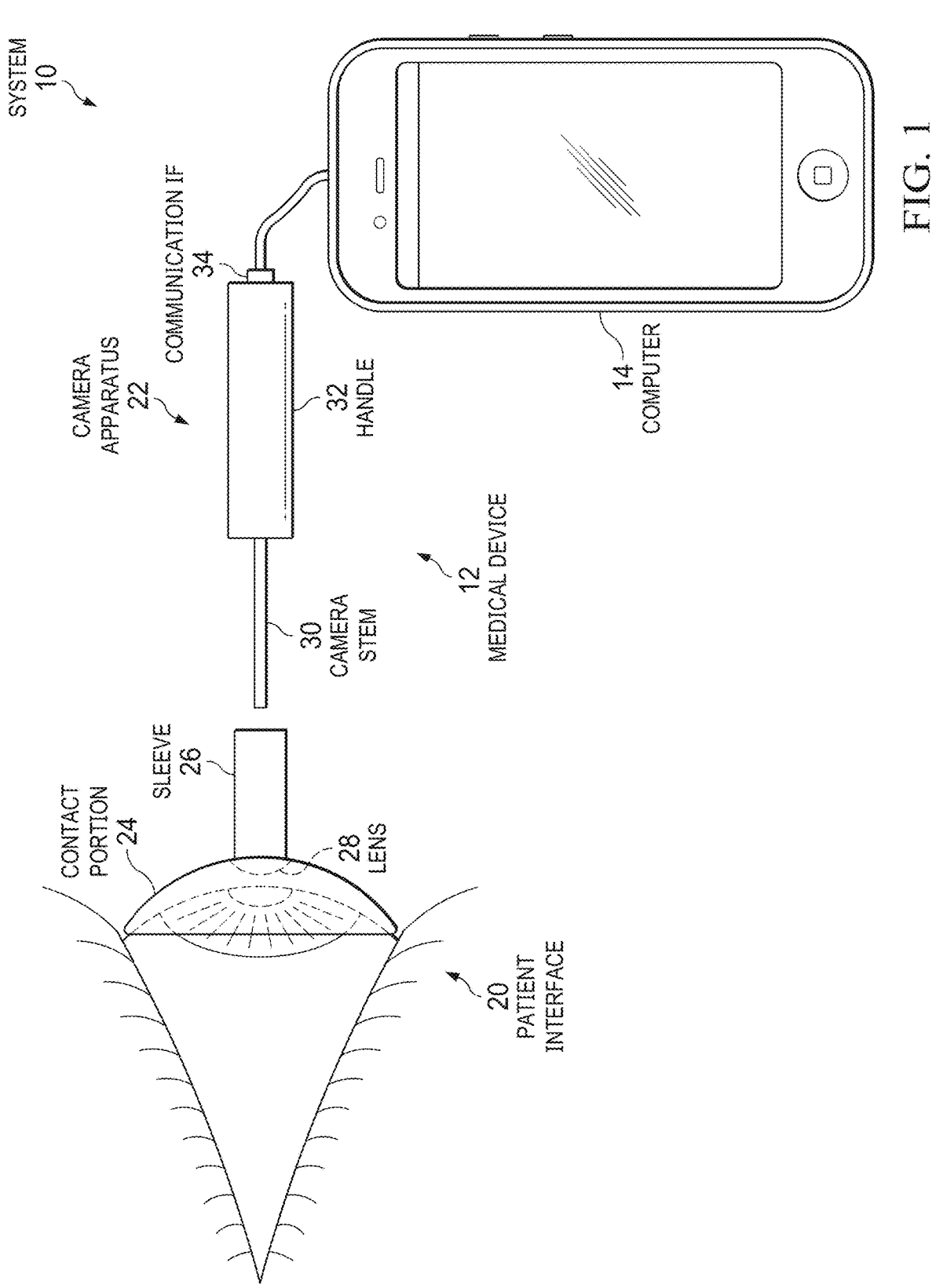
FIG. 1 illustrates an example of a system with a medical device that can generate image data for an image of the interior of an eye, according to certain embodiments.

Referring now to the description and drawings, example embodiments of the disclosed apparatuses, systems, and methods are shown in detail. The description and drawings are not intended to be exhaustive or otherwise limit the claims to the specific embodiments shown in the drawings and disclosed in the description. Although the drawings represent possible embodiments, the drawings are not necessarily to scale and certain features may be simplified, exaggerated, removed, or partially sectioned to better illustrate the embodiments.

Taking images of the retina of a patient's eye may be uncomfortable or even scary for the patient. Accordingly, embodiments of the system described herein include a patient interface that fits comfortably onto the eye. The patient interface includes a sleeve that receives the stem of a camera apparatus that generates image data for a retinal image. The camera apparatus has a communication interface that provides the image data to a computer (e.g., a smart phone), which can display the retinal image using the image data. The computer may have a software application that can be used to view or edit the image.

FIG. 1 illustrates an example of a system 10 with a medical device 12 that can generate image data for an image of the interior of an eye, according to certain embodiments. As an overview, system 10 includes medical device 12 and a computer 14, such as a smart phone, coupled as shown. Medical device 12 includes a patient interface 20 and a camera apparatus 22. Patient interface 20 includes a contact portion 24, a sleeve 26, and a lens 28 in some embodiments, coupled as shown. Camera apparatus 22 includes a camera stem 30, a handle 32, and a communication interface 34, coupled as shown.

As an overview of operation, contact portion 24 of patient interface 20 is coupled onto the anterior surface of an eye to facilitate stabilizing the eye relative to camera stem 30. Sleeve 26 of patient interface 20 receives camera stem 30 of camera apparatus 22. Illuminators of camera stem 30 emit light. Lens 28 of patient interface 20 transmits the light towards the interior of the eye, which reflects the light. Lens 28 transmits the reflected light towards an imaging subsystem of the camera apparatus 22, which generates a signal in response to detecting the reflected light. (In certain embodiments where an opening replaces lens 28, the opening passes through the light to and from the eye.) A processor generates image data for an image of the eye interior from the signal. Communication interface 34 sends the image data to computer 14 (e.g., a smart phone, a tablet computer, a laptop computer, or a desktop computer), which displays the image of the eye interior generated according to the image data. The image may comprise a single frame, such as a photograph, or multiple frames, such as a video.

Figure 2A:
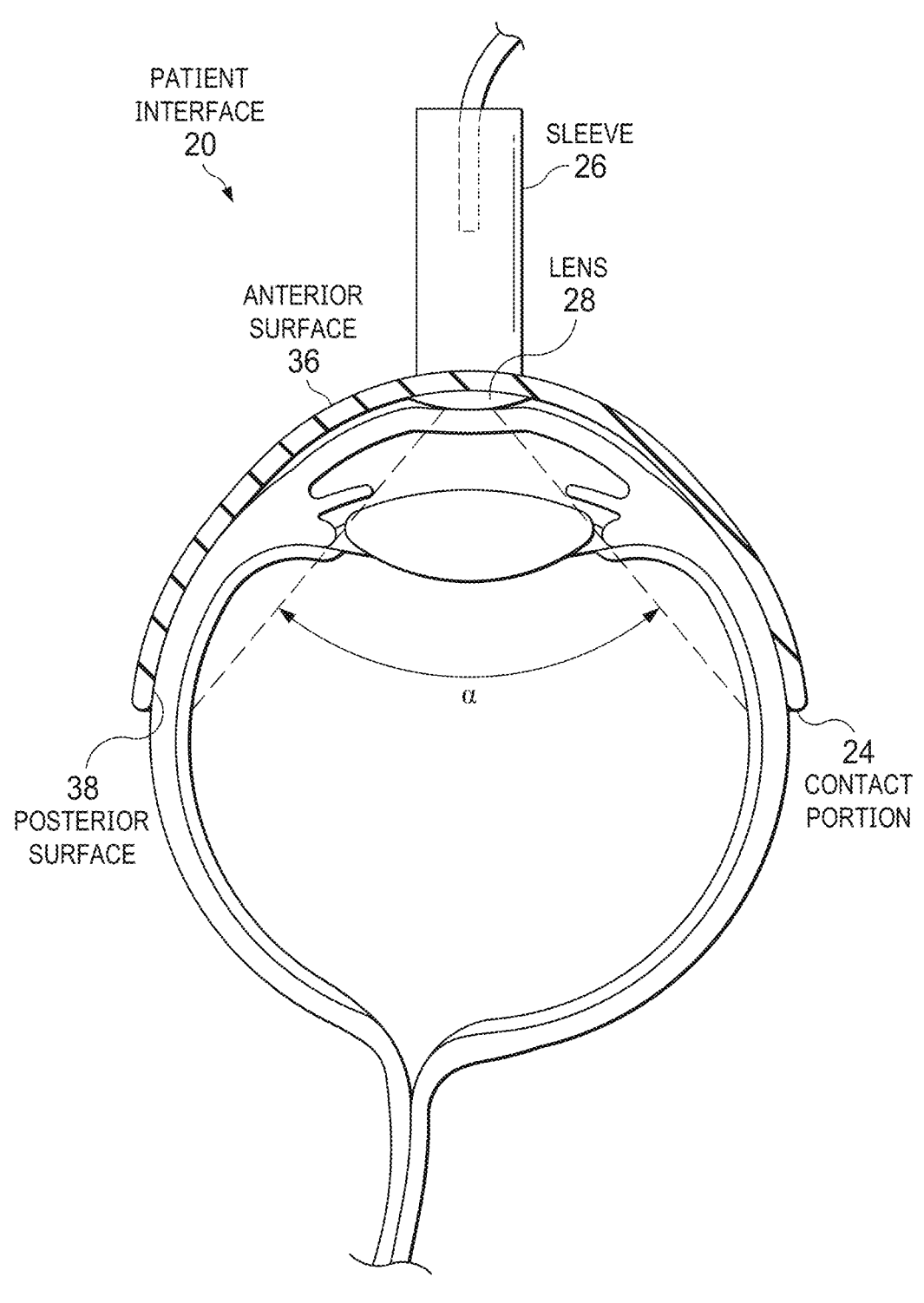
FIGS. 2A through 2F illustrate examples of patient interfaces of the medical device of FIG. 1, according to certain embodiments.
Figure 2B:
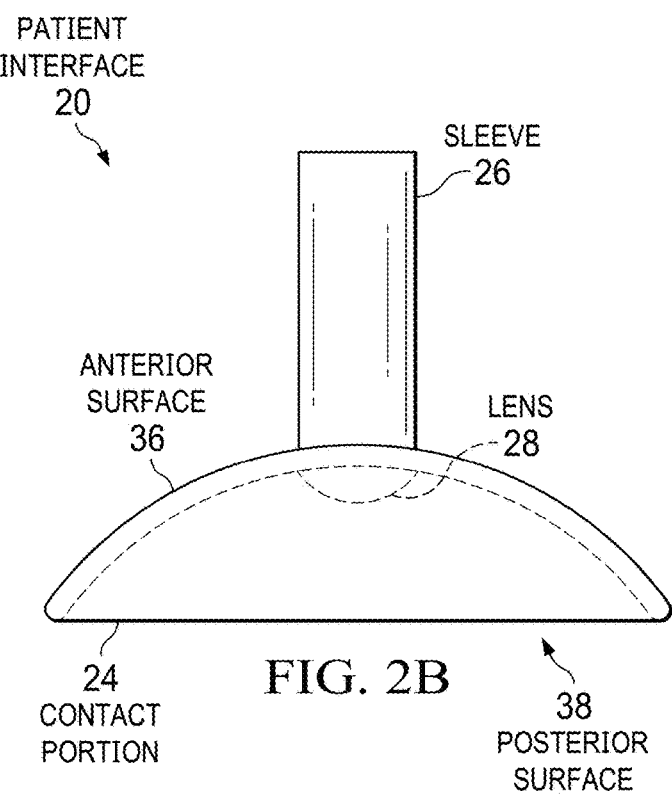
Figure 2C:
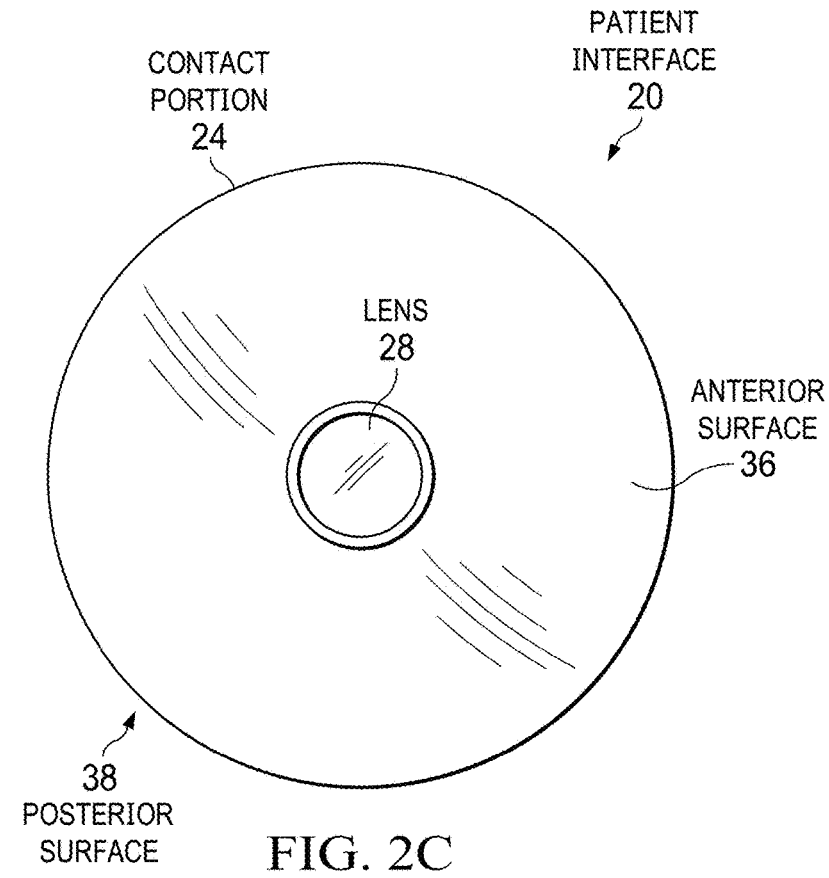
Figure 2D:
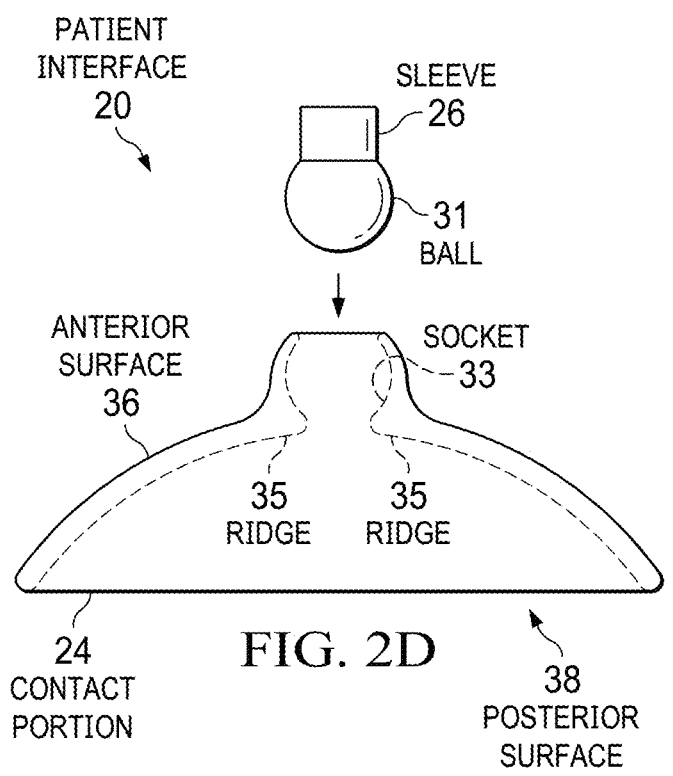
Figure 2E:
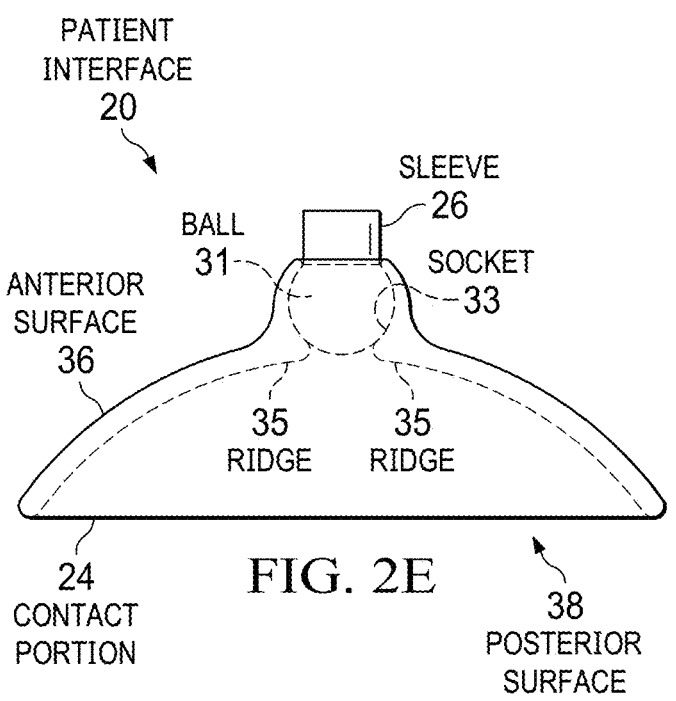
Figure 2F:
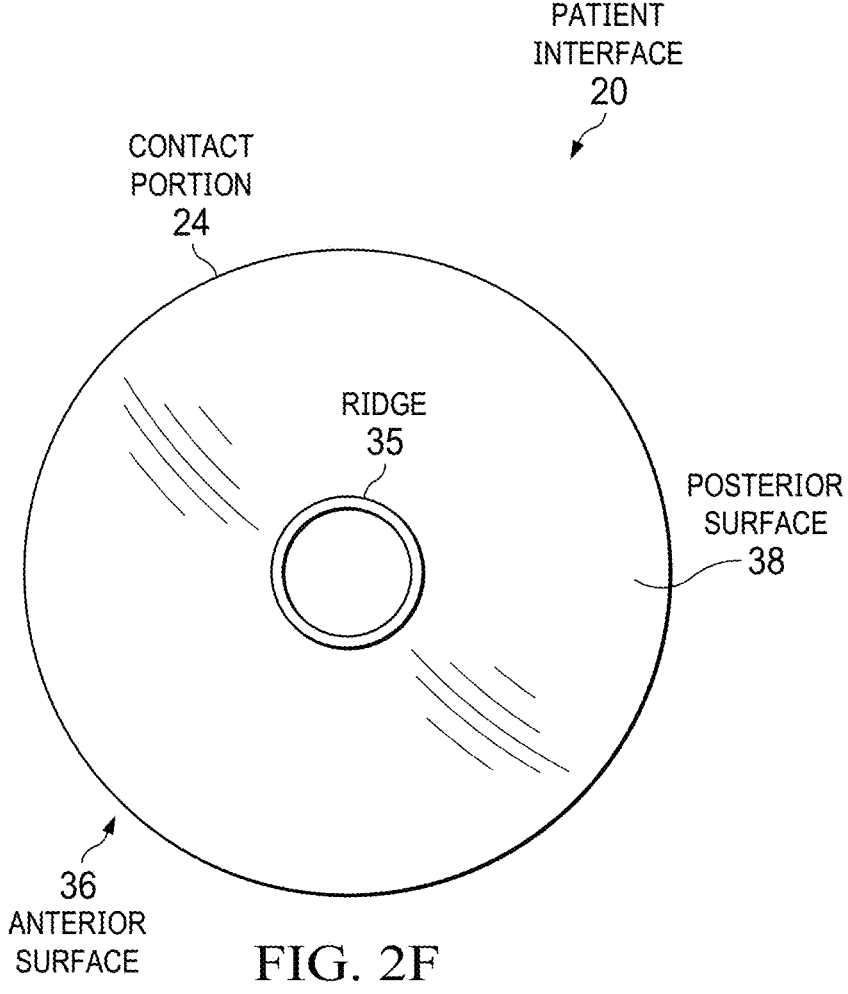

FIGS. 2A through 2F illustrate examples of patient interface 20 of medical device 12 of FIG. 1, according to certain embodiments. FIG. 2A shows patient interface 20 coupled to a patient eye. FIGS. 2B and 2C show a side view and an anterior view, respectively, of an example of patient interface 20. FIGS. 2D and 2F show side views and an anterior view, respectively, of another example of patient interface 20. In certain embodiments, patient interface 20 is a one-time-use interface that is disposed of after use with a patient. In other embodiments, patient interface 20 is a multiple-use interface that can be sterilized after use with a patient to be used for another patient.

In the example, contact portion 24 has an anterior surface 36 and a posterior surface 38. Contact portion 24 may have any suitable size and shape for coupling to the anterior surface of an eye. In certain embodiments, posterior surface 38 is shaped to conform to the anterior surface of the eye, e.g., has a concave shape. In certain embodiments, contact portion 24 has a diameter that is larger than (e.g., up to 10 millimeters (mm) larger than) the diameter of the average iris (e.g., 10 to 13 mm) of the target patient population. For example, the diameter of contact portion 24 may be in a range of 15 to 25 mm. Contact portion 24 may be specifically sized for patients of particular ages, e.g., a smaller interface 20 may be used for newborn patients and a larger interface 20 may be used for adult patients. For example, contact portion 24 may be come in different sizes, such as with small (e.g., 15 to 18 mm, such as 16 mm), medium (e.g., 18 to 22 mm, such as 20 mm), and large (e.g., 22 to 26 mm, such as 24 mm) diameters. Contact portion 24 may be made of any suitable transparent or opaque material, e.g., silicone or acrylic. In some examples, portion 24 is flexible and gives slightly when in contact with the cornea. In other examples, portion 24 is rigid.

Sleeve 26 is disposed outwardly from the central portion of anterior surface 34 of contact portion 24. Sleeve 26 may have any suitable size and shape to receive camera stem 30.

For example, sleeve 26 may have a cylindrical shape with any suitable diameter and length. For example, the diameter may be selected to accommodate camera stem 30, e.g., a diameter 0.1 to 5 mm larger than that of stem 30, such as a diameter of 3.1 mm to accommodate a stem 30 with a 3.0 mm diameter. The length may be selected to stabilize camera stem 30, e.g., a length in the range of 1 to 10, 10 to 20, 20 to 30, and/or 30 to 40 mm. Sleeve 26 may be coupled to contact portion 24 or sleeve 26 and contact portion 24 may be formed as one piece. Sleeve 26 directs light between the interior of the eye and camera stem 30 by, e.g., providing a passageway for the light.

FIGS. 2B and 2C illustrate an example of patient interface 20 with a lens 28 disposed within the central portion of contact portion 24. Lens 28 may be any suitable optical lens that can transmit light from the illuminators of camera stem 30 towards the interior of the eye, and transmit light reflected from the interior of the eye towards the objective lens system of camera stem 30. In certain embodiments, lens 28 may be a wide-angle lens with an angle α of view in the range of 64 to 84 degrees or an ultrawide-angle lens with an angle α of view in the range of 84 to 180 degrees.

FIGS. 2D through 2F illustrate an example of patient interface 20 with a ball 31 and socket 33 coupling. In the example, the posterior end of sleeve 26 is shaped like a ball 31, and anterior surface 36 of contact portion 24 has a socket 33 shaped to receive and fit ball 31. In certain embodiments, ball 31 may pop into and out of socket 33. Ball 31 and socket 33 allow camera stem 30 to slide into sleeve 26 and rotate within socket 33 to capture images with an angle of view up to 120, 240, or even 360 degrees. In certain embodiments, the posterior portion of socket 33 is open to the eye. The opening may, e.g., allow for an optical gel to be placed onto the eye. A ridge 35, disposed within socket 33 of sleeve 26, may prevent ball 31 from reaching the eye. Ridge 35 may circumscribe the opening and may, in certain embodiments, have one or more gaps, yet still prevent ball 31 from touching the eye.

Figure 3A:
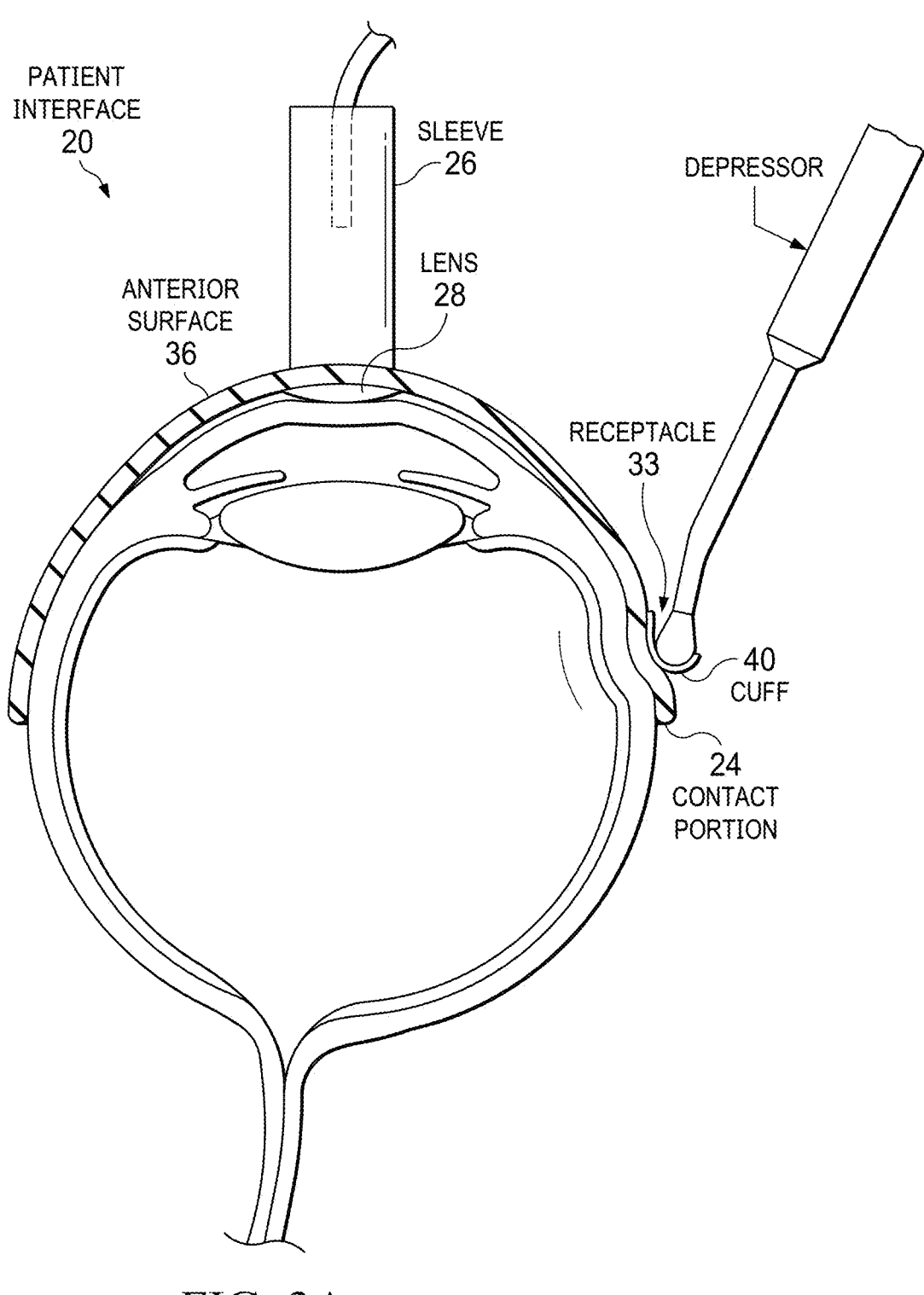
FIGS. 3A through 3C illustrate another example of a patient interface, which includes a cuff used to facilitate a scleral depression examination, according to certain embodiments.
Figures 3B, 3C:
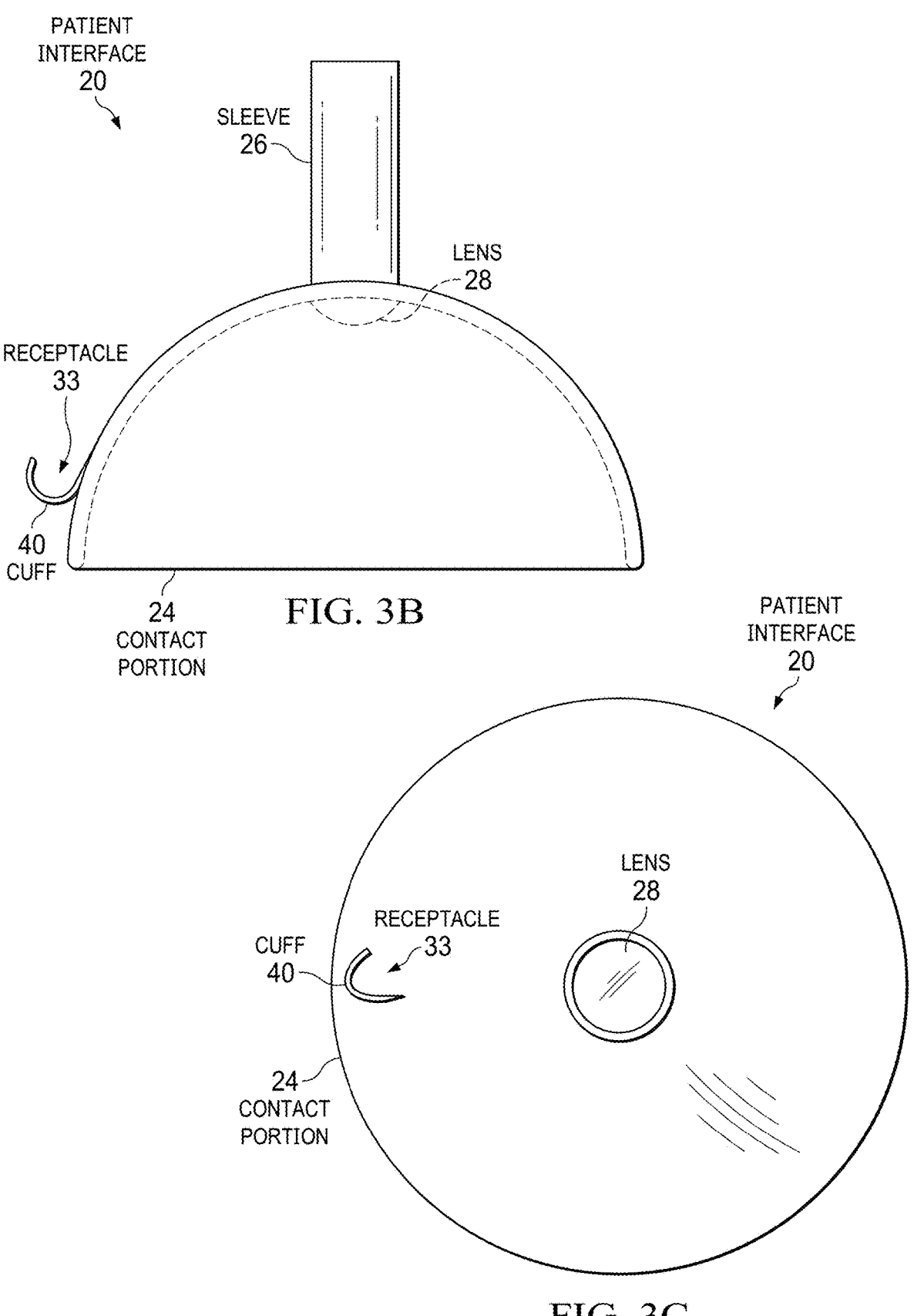

FIGS. 3A through 3C illustrate another example of patient interface 20, which includes a cuff 40 that may be used to facilitate scleral depression during a retinal examination procedure, according to certain embodiments. FIG. 3A illustrates an example of the procedure, which may be used to improve images of the peripheral fundus near the pars plana and ora serrata. In the procedure, the tip of a scleral depressor is inserted into cuff 40, which allows the tip to depress a region of the sclera. This action displaces the peripheral retina inward and creates an elevation, enhancing the contrast between the region and the surrounding retinal tissue to improve imaging of the region. In certain embodiments, cuff 40 may allow the scleral depressor to move (e.g., rotate) contact portion to another region of the retina to improve imaging of that region.

Cuff 40 is disposed outwardly from anterior surface 36 of contact portion 24 of patient interface 20. In certain embodiments, cuff 40 forms a receptacle 33 into which a scleral depressor can be inserted into in order to depress the sclera and to rotate contact portion 24. In certain embodiments, cuff 40 may be placed in an area of contact portion 24 that is placed over the sclera of the patient eye to depress the peripheral retina. Cuff 40 may have any suitable size and shape that can accommodate the tip of a scleral depressor to perform a scleral depression procedure. For example, cuff 40 may form receptacle 33 for a space slightly (e.g., 1 to 5 mm) larger than the depressor tip. Also, cuff 40 may form a barrier to which the depressor can apply a force to rotate contact portion 24. In certain embodiments, the diameter of contact portion 24 may be larger to accommodate cuff 40, such as 3 to 7 mm (e.g., 5 mm) larger than the diameters described with reference to FIG. 2A.

FIG. 3B is a side view and FIG. 3C is an anterior view of an example of a cuff 40. In the example, cuff 40 is a hook-shaped protrusion that forms receptacle 33 into which a scleral depressor can be inserted into to depress the peripheral retina and to rotate contact portion 24. Cuff 40, however, may have other embodiments. For example, cuff 40 may have a different shape, e.g., a cylinder, a cup, or a depression.

FIGS. 2A through 3C illustrate examples of patient interface 20. One skilled in the art will recognize that other patient interfaces 20 may include features from different examples. For example, a patient interface 20 may have a ball-and-socket sleeve 26 and/or a lens 28 and/or a cuff 40, or a patient interface 20 may have a non-ball-and-socket sleeve 26 (e.g., like in FIG. 2B) and/or a lens 28 and/or a cuff 40. That is, a patient interface 20 may have a ball-and-socket sleeve 26, a lens 28 or an opening, and a cuff 40 or no cuff 40 (e.g., like in FIG. 2B). Alternatively, a patient interface 20 may have a non-ball-and-socket sleeve 26, a lens 28 or an opening, and a cuff 40 or no cuff 40.

Figures 4A, 4C:
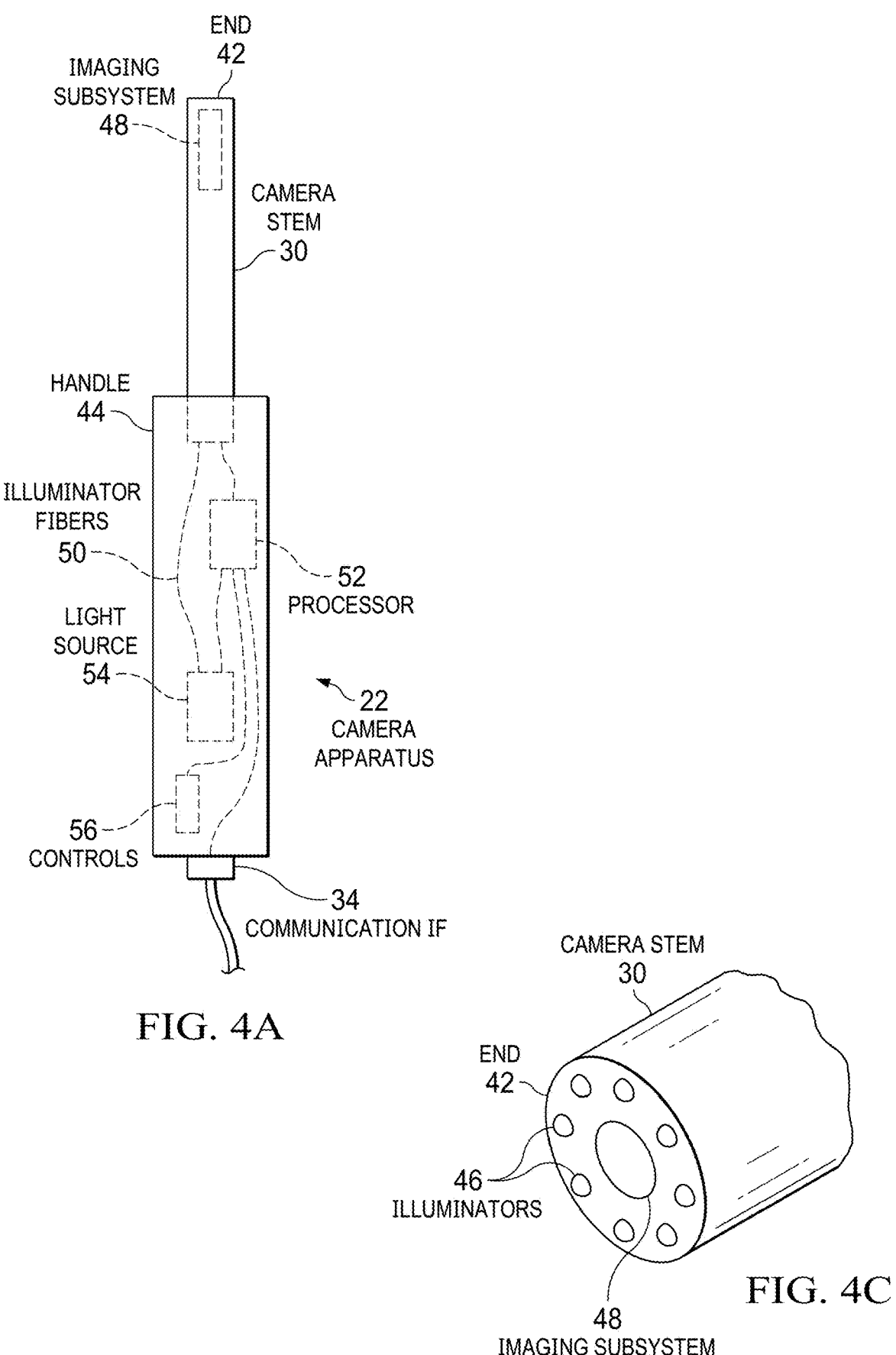
FIGS. 4A though 4C illustrate an example of a camera apparatus of the medical device of FIG. 1, according to certain embodiments.
Figure 4B:
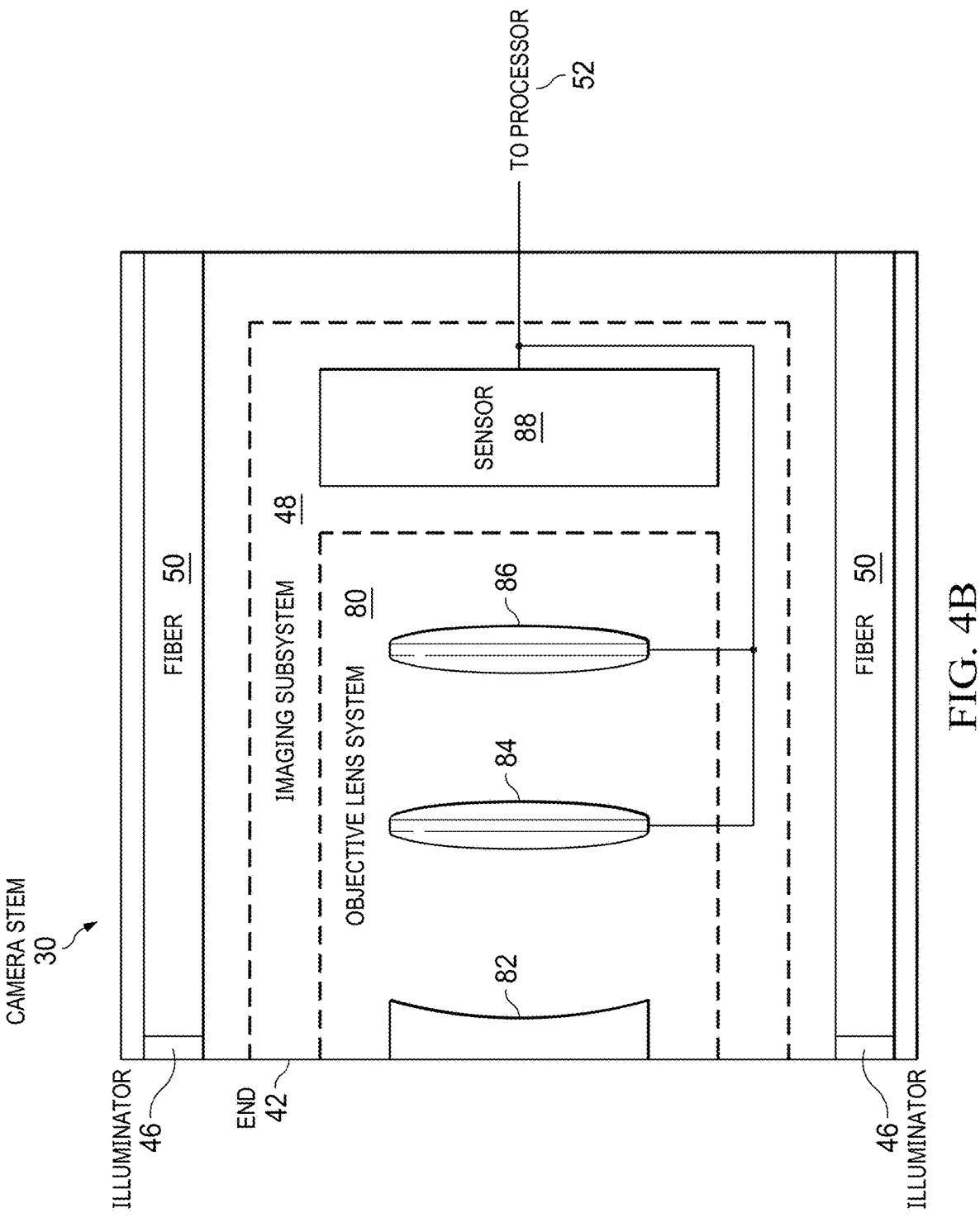

FIGS. 4A though 4C illustrate an example of camera apparatus 22 of medical device 12 of FIG. 1, according to certain embodiments. FIG. 4A illustrates camera apparatus 22, FIG. 4B illustrates camera stem 30 of camera apparatus 22, and FIG. 4C illustrates the distal end 42 of camera stem 30.

In the example, camera apparatus 22 includes camera stem 30 (with end 42) and handle 44, coupled as shown. Camera stem 30 includes illuminators 46, an imaging subsystem 48, and illuminator fibers 50, coupled as shown. Imaging system 48 includes an objective lens system 80 (which includes a receiving lens 82, a zoom lens 84, and a focus lens 86) and an image sensor 88. In the illustrated example, handle 44 includes illuminator fibers 50, a processor 52, a light source 54, controls 56, and communication interface 34, coupled as shown. In other examples, illuminators 46 of camera stem 30 include their own light source, e.g., illuminators 46 are LED lights, such that light source 54 and illuminator fibers 50 are not located in handle 44.

As an example of operation of the illustrated embodiment, light source 54 generates light, which travels through illumination fibers 50 and is emitted by illuminators 46. (In other examples, illuminators 46 may generate and emit light.) The light is directed into the interior of an eye and reflected by the interior. Objective lens system 48 receives the reflected light and transmits the light to camera sensor 88. Camera sensor 88 generates a signal in response to detecting the light, and processor 52 generates image data from the signal. Communication interface 34 provides the image data to, e.g., computer 14.

Turning to the details, camera stem 30 has a distal end 42 that can be inserted into sleeve 26 of patient interface 22. Camera stem 30 may be any suitable size and shape that can accommodate imaging system 48 and illuminators 46 (and, in some examples, illumination fibers 50) and can be inserted into sleeve 26. For example, camera stem 30 may have an elongated shape with a length of 1 to 5 centimeters (cm) (such as 2.5 cm) and a diameter of 1 to 20 mm (such as 3 mm). In certain embodiments, camera stem 30 is rigid and straight (comprising, e.g., a metal such as stainless steel), and the axis of stem 30 may be defined by the longitudinal axis of the elongated shape. In other embodiments, camera stem 30 is rigid with a bend, and the axis of stem 30 may be defined by the longitudinal axis of the elongated shape at end 42 to be inserted into sleeve 26. In yet other embodiments, camera stem 30 is flexible (comprising, e.g., a flexible plastic or metal) and can bend into a shape desired by user.

Camera stem 30 includes one or more illuminators 46 and imaging subsystem 48. Illuminators 46 emit light. In the illustrated embodiment, light source 54 of illuminators 46 is housed inside of handle 44, and illumination fibers 50 carry the light from source 54 to illuminator 46. In the embodiment, light source 54 may be a laser light, and illuminator fibers 50 may be optical fibers. In other embodiments, illuminators 46 include their own light source within camera stem 30, such as LED lights. An illuminator 46 may include a lens that diffuses the light.

Objective lens system 80 receives light reflected by and/or emitted by an object and modifies the light for image sensor 88. Receiving lens 82 (e.g., a fisheye lens) gathers the reflected and/or emitted light. Receiving lens 82 may have a focal length that corresponds to the average diameter of a human eye, which ranges from 16 mm for a premature infant to 27 mm for a large adult eye. For example, to screen ROP patients, the focal length may be 17 to 18 mm (e.g., 17.5 mm), corresponding to the average diameter of a premature infant's eye. Zoom lens 84 adjusts optical magnification, and focus lens 86 adjusts the focal distance. In certain embodiments, zoom lens 84 and focus lens 86 may be automatically adjusted by processor 52 to autofocus the camera at the object (e.g., the retina) according to, e.g., a contrast or phase detection autofocus technique. Image sensor 88 may be an array of photosensors (e.g., a charge-coupled device CCD sensor) that detects light reflected and/or emitted by an object. In response to detecting light, image sensor 88 generates a signal that records the pattern of detected light. The signal is provided to processor 52, which processes the signal to generate image data used to display an image of the object.

Handle 44 may be any suitable handheld size and shape that can accommodate processor 52 (and in some examples illumination fibers 50 and/or light source 54) and can support user controls 56. In certain embodiments, handle 44 is an elongated shape, such as a cylinder, with a handle axis in the lengthwise direction. The cylinder may have any suitable cross-section, such as circular or polygonal (e.g., pentagonal). For example, handle 44 may have an elongated shape with a length of 1 to 10 cm (such as 6 cm) and a diameter of 3 to 20 mm (such as 10 mm). In certain embodiments, handle 44 has a rubberized polymer surface that allows the user to easily grip handle 44.

User controls 56 include user controllers (e.g., buttons, sliders, and/or toggles) that allow the user to control image acquisition. A user controller receives an instruction from the user to perform an action and provides the instruction to processor 52 to perform the action. As an example, a user controller may be used to change the focus, zoom, and/or magnification by adjusting one or more lenses of objective lens system 80 (e.g., receiving lens 82, zoom lens 84, and/or focus lens 86). As another example, a user controller may be used to adjust the light intensity of illuminators 46. As another example, a user controller may be used to control (e.g., starting, pausing, or stopping) video image capture.

Processor 52 performs computing operations for camera apparatus 22. For example, processor 52 processes the signal from image sensor 88 to generate image data, which may be sent to computer 14 to display an image of the object. As another example, processor 52 receives an instruction from the user via user controls 56 and then controls components of camera apparatus 22 to the instructed operation.

In certain embodiments, camera apparatus 22 includes an autofocus system, such as an active or passive autofocus system. The autofocus system determines the distance to the subject and adjusts one or more lenses to move the focal point to the location of the subject such that the subject is in focus. In an active autofocus system, an emitter emits a signal (e.g., a soundwave or infrared wave), a sensor (such as a part of sensor 88) detects the signal reflected from the subject, and processor 52 measures the distance according to the travel time of the signal. In a passive autofocus system, processor 52 analyzes images taken a different focal points and searches for the point of best focus, e.g., the point where there is maximum intensity difference between adjacent pixels.

In certain embodiments, camera apparatus 22 (e.g., objective lens system 80) receives light reflected by and/or emitted by the eye object and transmits the light to a camera of computer 14. In an example, objective lens system 80 is optically coupled to a light pipe (e.g., an optical fiber) that passes through handle 44 and is optically coupled to a camera within computer 14. Objective lens system 80 receives the light, and the light pipe delivers it to the camera.

Camera stem 30 and handle 44 of camera apparatus 22 may have any suitable configuration. Stem 30 and handle 44 may each have separate housings that are coupled together, or they may share the same housing. Stem 30 and handle 44 may have any suitable orientation relative to each other. In certain embodiments, the stem axis may be aligned with handle axis, or may be at an angle in the range of 10 to 45 degrees relative to the handle axis. In certain embodiments, camera apparatus 22 is watertight to allow for submersible cleaning.

Communication interface 34 outputs the image data. In certain embodiments, communication interface 34 may provide a wired and/or wireless communication link. The wired communication link may be, e.g., a communication cable (e.g., a lightning and/or universal serial bus (USB) cable) or a port that accepts a communication cable (e.g., a USB port). The wireless communication link and may be, e.g., a transceiver such as a Bluetooth antenna.

FIGS. 5A to 5E illustrate examples of a graphical user interface (GUI) 60 for processing a retinal image that may be displayed by computer 14 of FIG. 1, according to certain embodiments. A retinal image may comprise a single frame, such as a photograph, or multiple frames, such as a video. Computer 14 may include or have access to software that allows computer 14 to process and analyze a retinal image. Examples of such software include image processing and image analysis software.

Figure 5A:
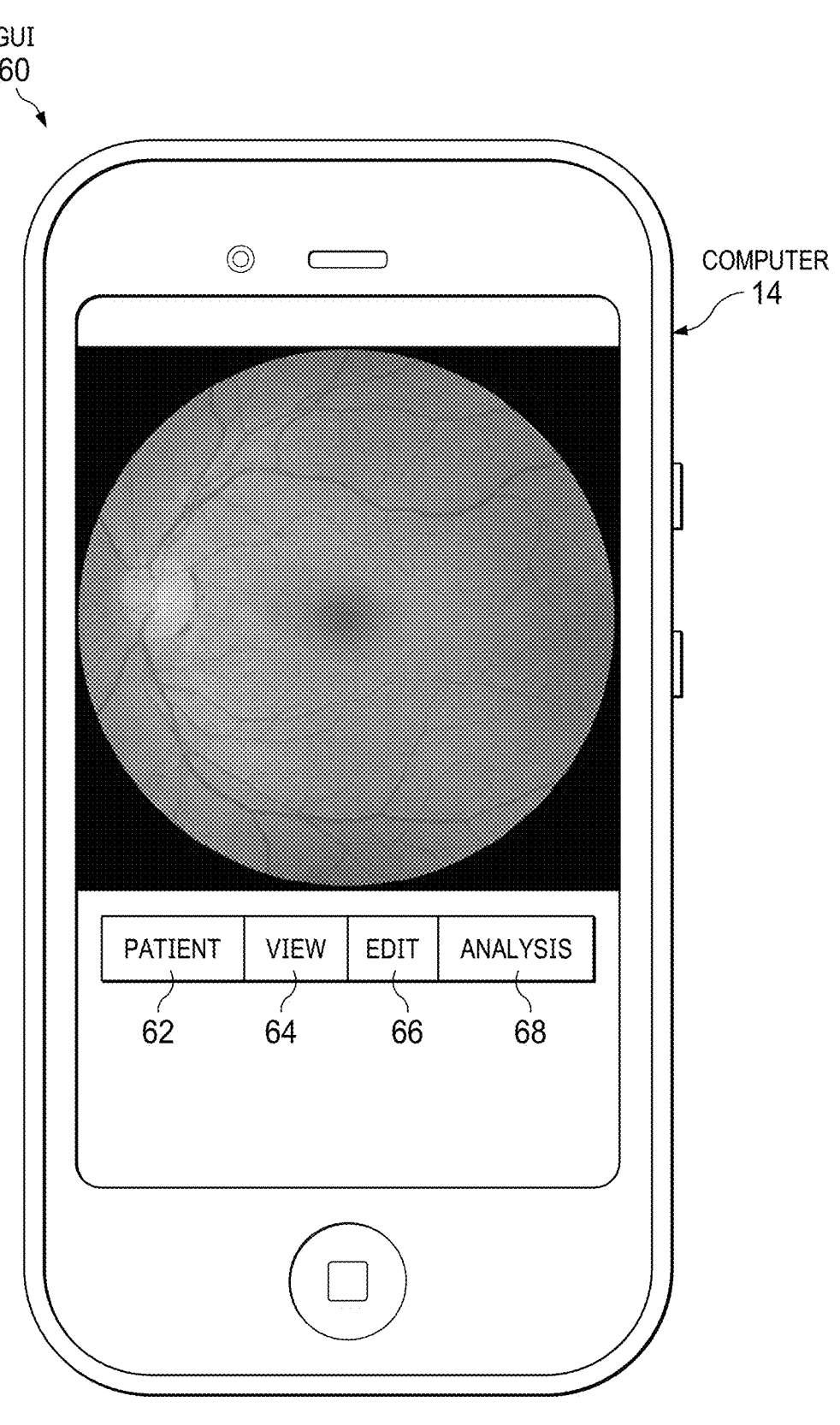
FIGS. 5A to 5E illustrate examples of a graphical user interface (GUI) for processing a retinal image that may be displayed by the computer of FIG. 1, according to certain embodiments.

FIG. 5A shows GUI 60 displaying options representing actions that facilitate analysis of a retinal image. The options include, e.g., patient data 62, image viewing 64, image editing 66, and/or image analysis 68 options. GUI 60 may present the options as selectable graphical elements, e.g., buttons, sliders, or menu items.

Figure 5B:
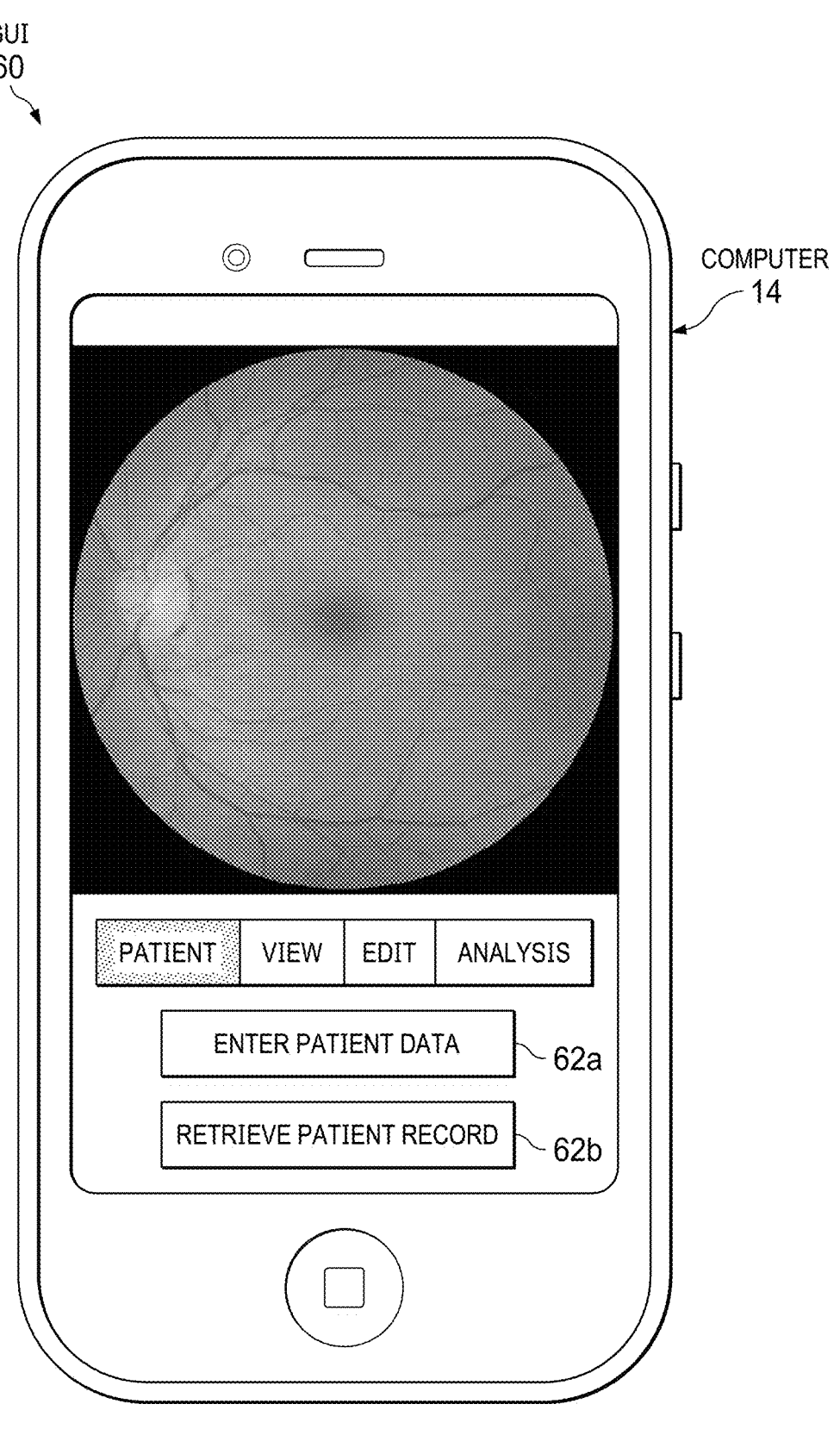

FIG. 5B shows GUI 60 displaying patient data options 62 (62a, 62b) designed to gather patient data, such as name, date of birth, birth weight, age at birth, and/or adjusted gestational age of the patient. Option 62a displays one or more patient data fields into which a user can enter patient data, and option 62b retrieves a stored patient record that includes patient data.

Figure 5C:
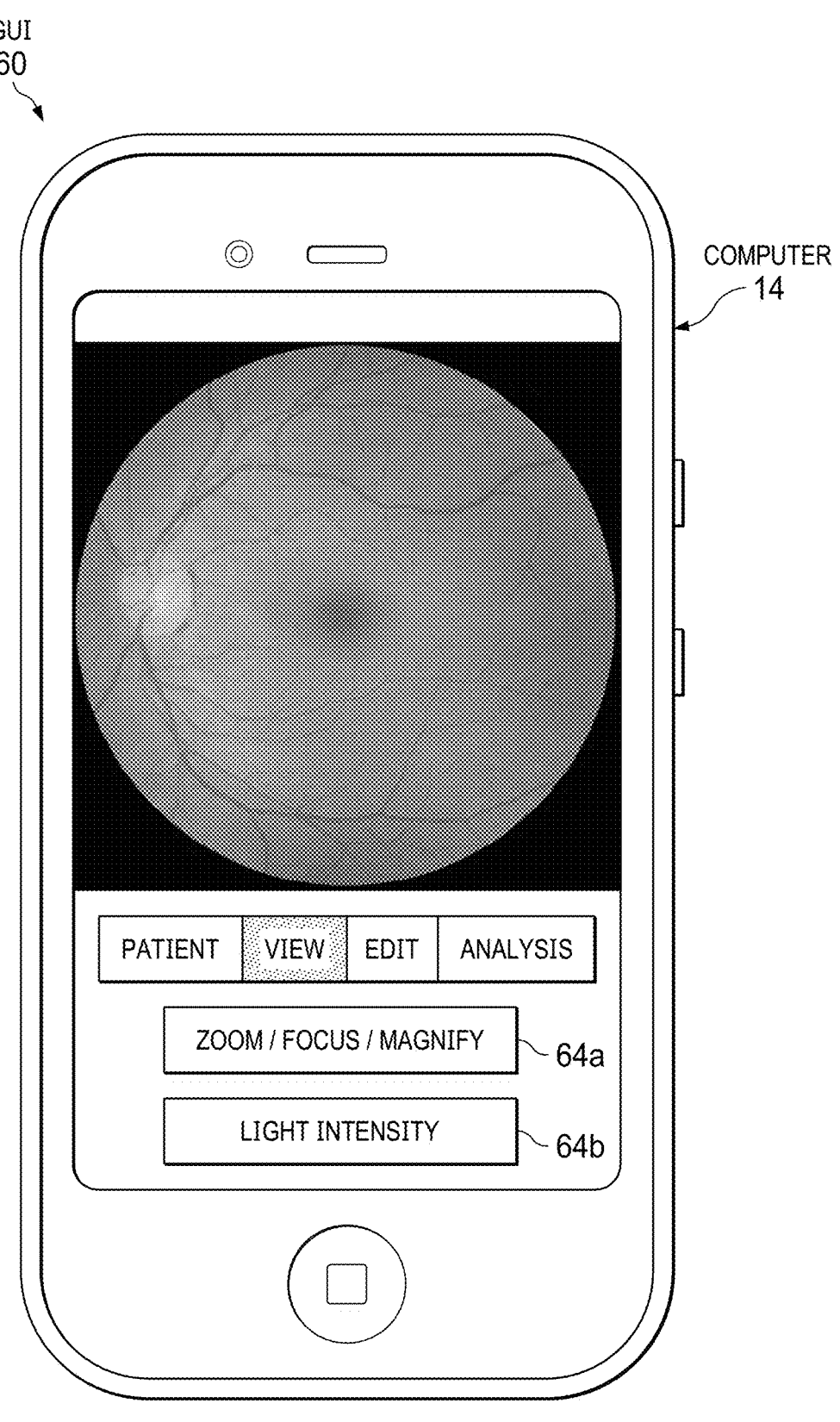

FIG. 5C shows GUI 60 displaying image viewing options 64 (64a, 64b) designed to adjust the view of a retinal image. If the image is live, viewing options 64 may control focus and/or zoom lenses of objective lens system 80 to change the view. If the image is recorded, viewing options 64 may manipulate image data of the image to adjust the view. Option 64a allows the user to zoom, focus, and/or magnify at least a portion of the image. For example, the user may select (e.g., by touching) a portion of the screen and then option 64a zooms in on, focuses, and/or magnifies that portion. The zooming, focusing, and/or magnifying may be automatic, or option 64a may display a graphical element (e.g., a slider) that allows the user to manually zoom, focus, and/or magnify. Option 64b presents selectable graphical elements to adjust the light intensity of the image.

Figure 5D:
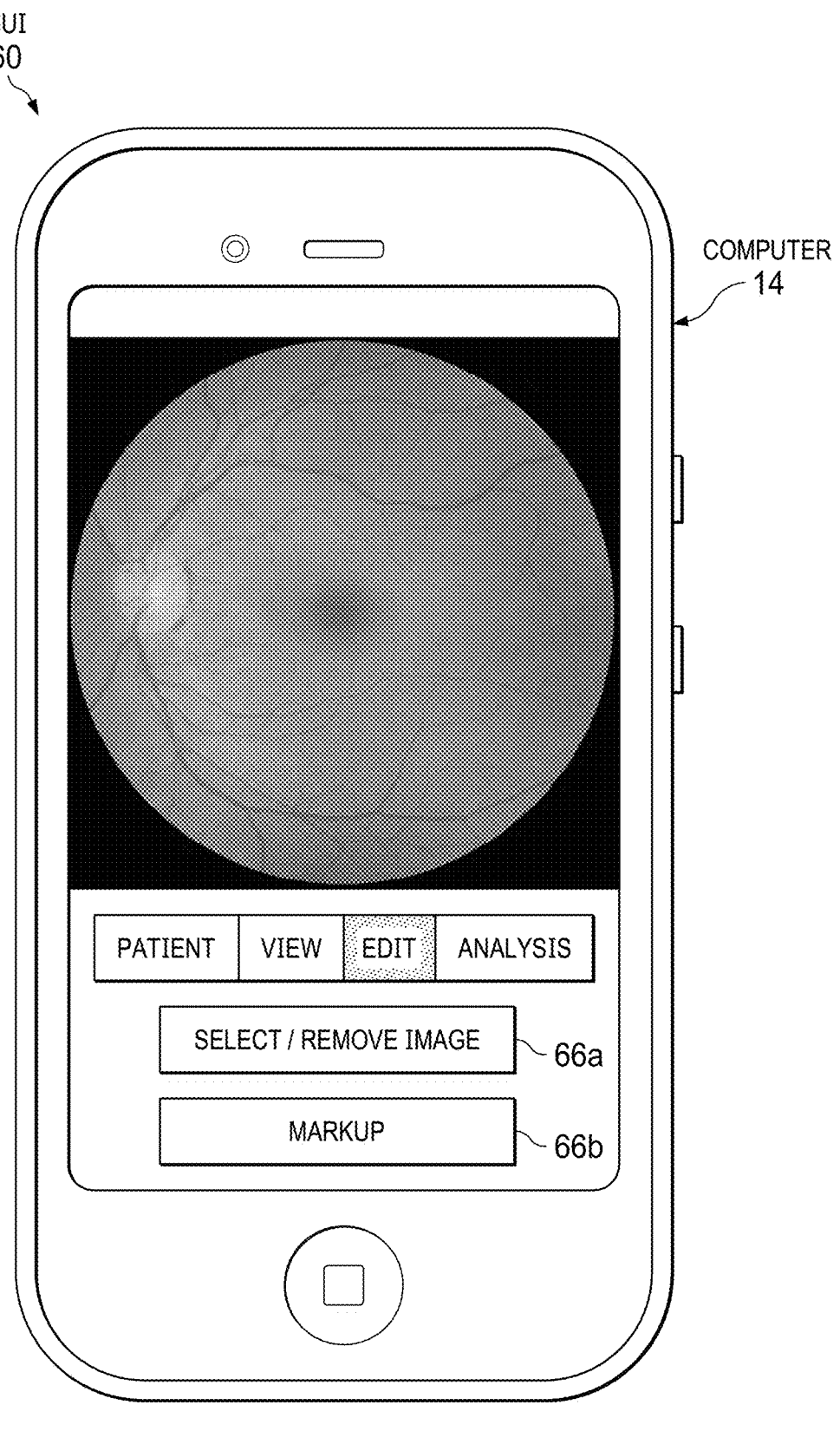

FIG. 5D shows GUI 60 displaying image editing options 66 (66a, 66b) designed to modify a retinal image. Option 66a allows the user to select to capture one or more retinal image frames from a video of the retinal image and remove the selected frame(s) or save the selected frame(s) as a photograph or a video. Option 66a may allow the user to speed up, slow down, or even stop the rate of playing the video. Option 66b allows the user to mark up an image, e.g., draw markings with a finger or stylus on the image or enter text onto the image.

Figure 5E:
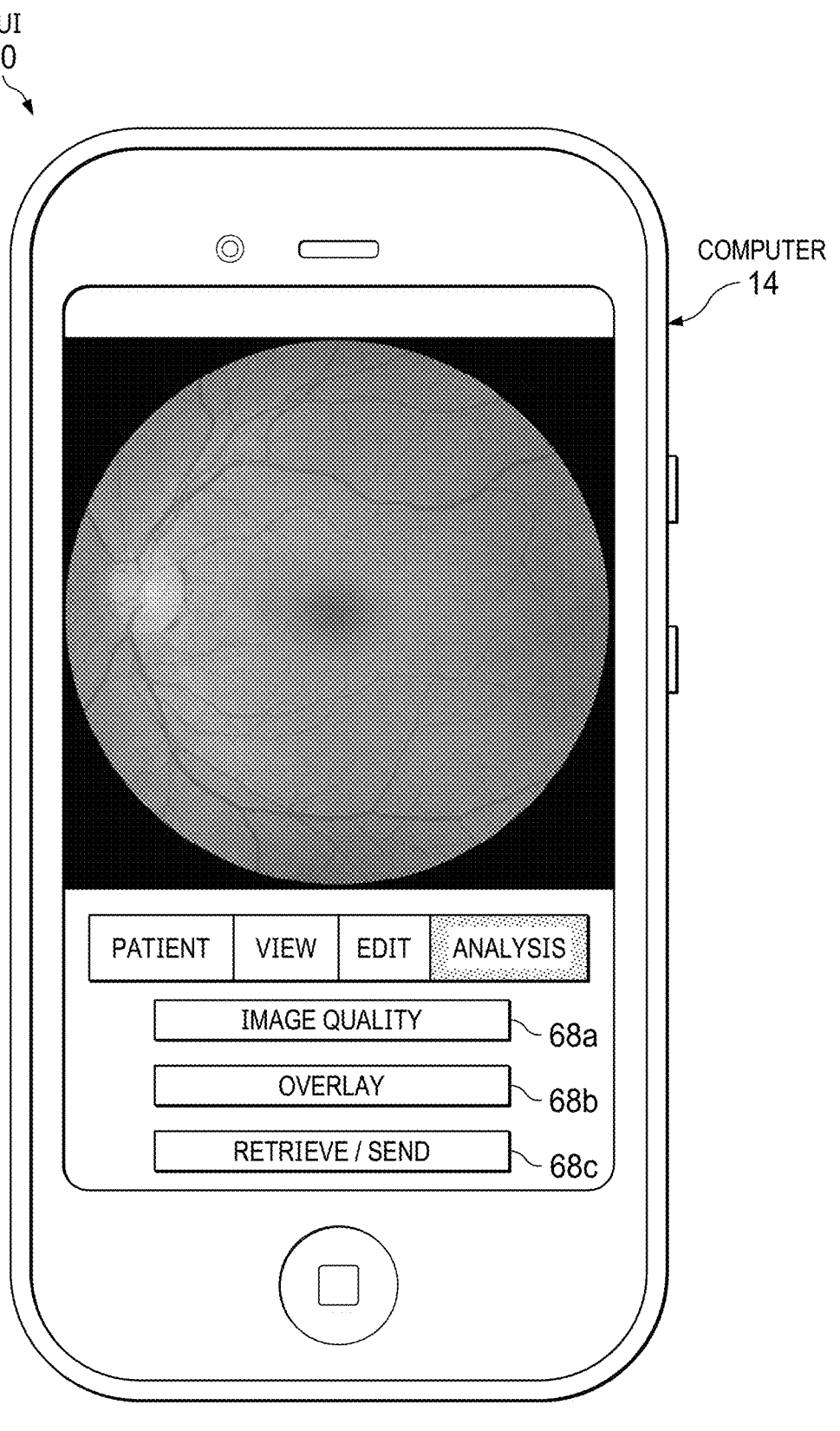
Figure 5F:
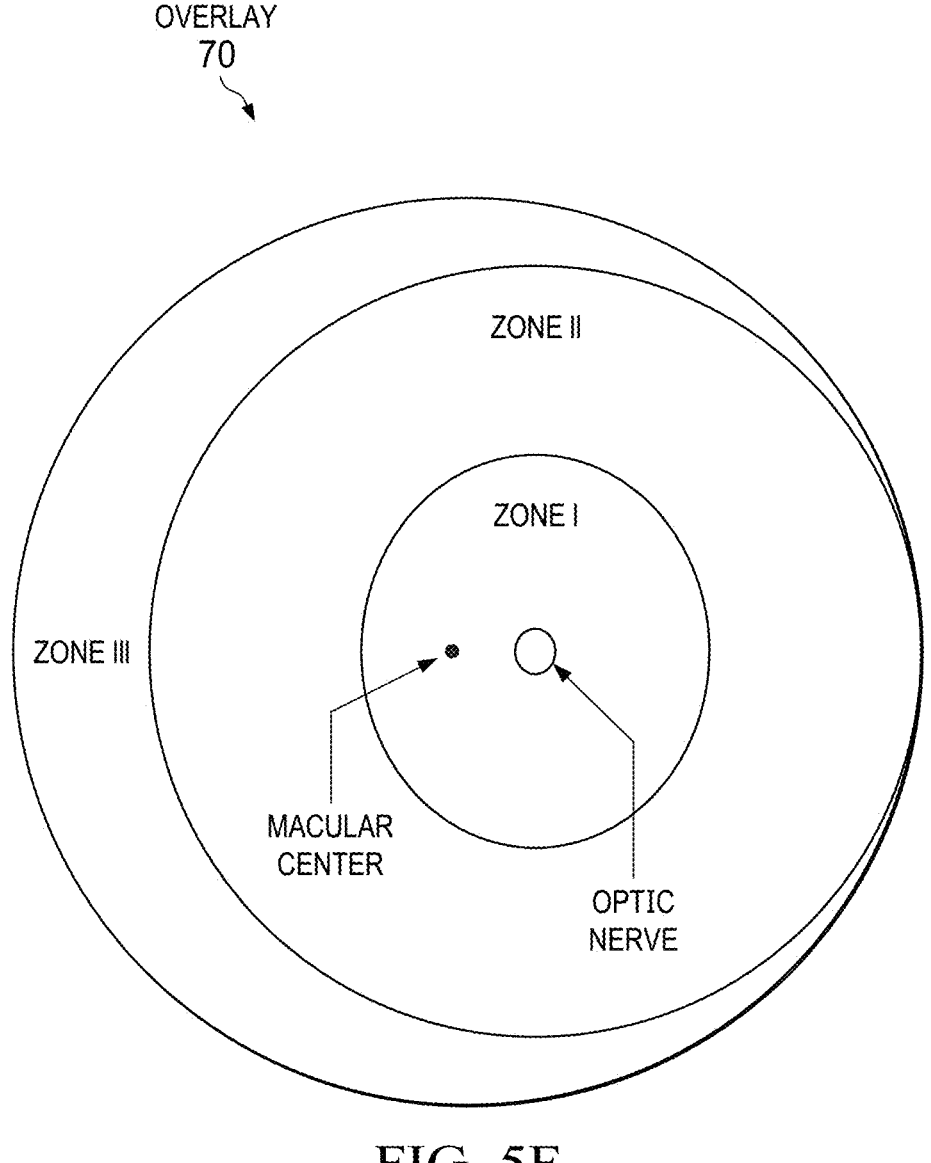
FIG. 5F illustrates an example of a graphical overlay that may be superimposed onto a retinal image.

FIG. 5E shows GUI 60 displaying image analysis options 68 (68a, 68b) designed to analyze a retinal image for a retinopathy. Option 68a instructs computer 14 to check the image quality (e.g., sharpness, noise, tone, and dynamic range) of a retinal image using, e.g., image processing software. The retinal image may be required to satisfy a predefined minimal image quality. Option 68b presents options of graphical overlays that can be superimposed onto a retinal image. The overlay may describe patient data or indicate a feature of the retina. FIG. 5F describes an example of an overlay 70. Option 68c allows the user to retrieve and/or send information such as patient data or video images. For example, option 68c allows the user to retrieve previously acquired images from the same patient to compare with the currently acquired images. As another example, option 68c allows the user to export images to, e.g., electronic mail, an electronic folder, or a database, for access by other parties.

FIG. 5F illustrates an example of a graphical overlay 70 that may be superimposed onto a retinal image. In the example, overlay 70 presents zones of the retina, as described in the International Classification of Retinopathy of Prematurity (ICROP). ICROP includes parameters to describe ROP, such as the zone of the disease, the circumferential extent of the disease, and the severity of the disease.

Overlay 70 superimposes the ICROP zones into a retinal image, where the zones are centered on the optic nerve. Zone I is the posterior zone of the retina defined by a circle with a radius extending from the optic nerve to double the distance to the macula. Zone II is an annular region with the inner border defined by Zone I and the outer border defined by a circle with a radius extending from the optic nerve to the nasal ora serrata. Zone III is the remaining temporal crescent of the retina.

In certain embodiments, computer 14 uses image analysis, e.g., edge and/or color detection, to superimpose overlay 70 onto a retinal image. In the embodiments, computer 14 may use image analysis to detect the optic nerve head (ONH) (or optic disk) and the oval-shaped macula in a retinal image to center Zone I of overlay 70. Zone II may be sized in accordance with Zone I, e.g., the average size of Zone II that typically appears with given Zone I may be used. The remaining region of the retina may be defined as Zone III.

FIG. 6 illustrates an example of a method for capturing an image of the interior of a patient eye, according to certain embodiments. The method may be performed by medical device 12 of FIG. 1, which includes a patient interface and a camera apparatus. The patient interface includes a contact portion (which may include a lens) and sleeve. The camera apparatus includes a camera stem (with illuminators) and a camera (with an imaging system and a processor).

The method starts at step 210, where the contact portion of the patient interface couples to the anterior eye surface of the eye. The sleeve of the patient interface receives the camera stem of the camera apparatus at step 212. Illuminators of the camera stem emit light at step 214 to illuminate the interior of the eye. Illuminators may include, e.g., one or more LED lights or a system with a light source and one or more illuminator fibers. An opening or a lens of the patient interface transmits the light towards the eye interior at step 216. The eye interior reflects the light.

The opening or lens transmits reflected light from the eye interior towards the camera of the camera apparatus at step 220. The camera generates image data in response to the reflected light at step 222. The image data can be used to generate an image of the eye interior. The camera sends the image data to a computer (e.g., a smart phone) at step 224 to generate and display the image. The method then ends.

Figure 7:
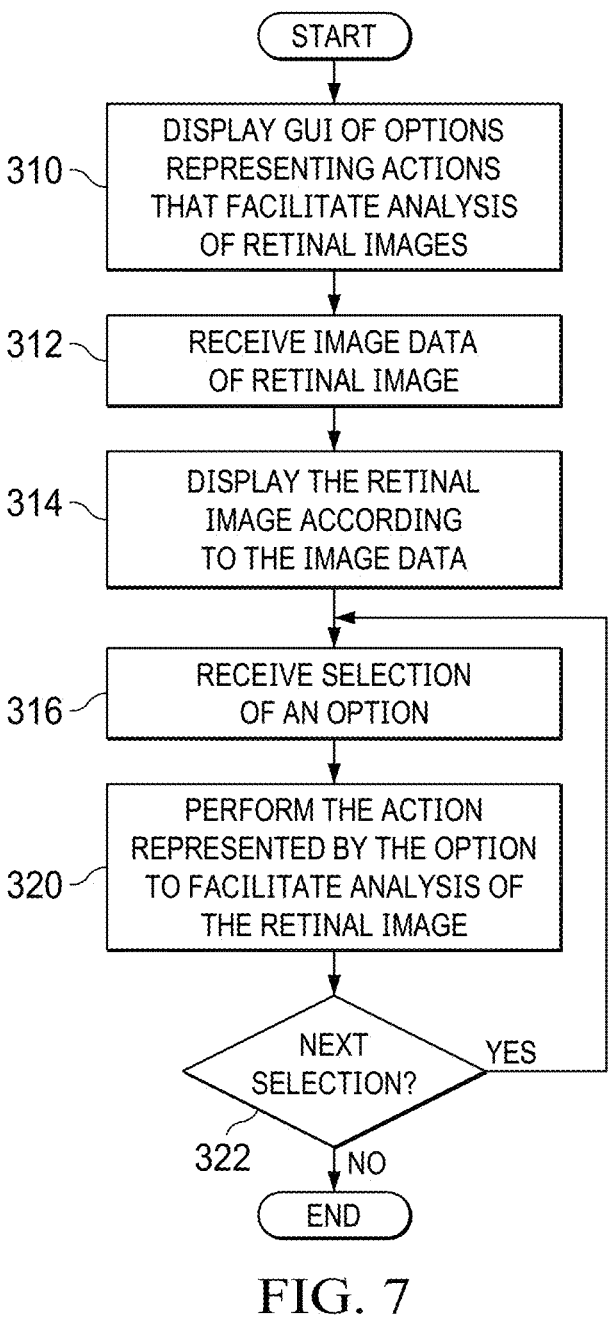
FIG. 7 illustrates an example of a method for analyzing retinal images generated from image data provided by the computer of FIG. 1, according to certain embodiments.

FIG. 7 illustrates an example of a method for analyzing retinal images that may be generated from image data provided by medical device 12 of FIG. 1, according to certain embodiments. The method may be performed by a computer, such as computer 14 of FIG. 1. The retinal image may comprise a single frame, such as a photograph, or multiple frames, such as a video.

The method starts at step 310, where a computer displays a GUI of options representing actions that facilitate analysis of retinal images. The action may facilitate, e.g., management of patient data (such as patient birth weight, age at birth, and/or gestational age), image viewing, image editing, and/or image analysis. The computer receives image data of a retinal image at step 312. The image data may be provided by a system that captures images of the retina, e.g., medical device 12 of FIG. 1. The computer displays the retinal image according to the image data at step 314.

The computer receives a selection of an option to facilitate analysis of the retinal image at step 316 and performs the action represented by the option at step 320. As an example, for a patient data option, the computer may gather patient data entered into a patient data field of the GUI and/or retrieve a stored patient record. As another example, for an image viewing option, the computer may zoom in on, focus, magnify, and/or adjust the light intensity of the retinal image. As yet another example, for an image editing option, the computer may save one or more frames from a video retinal image as a photograph or a new video, remove one or more frames from a video retinal image, and/or place a marking on a video or photograph retinal image. As yet another example, for an image analysis option, the computer may check the image quality of the retinal image or display an overlay onto the retinal image, where the overlay may describe patient data or indicate zones of the retina. A next option may be selected at step 322. If there is a next option, the method returns to step 316 to receive the next selection. If there is not, the method ends.

A component (such as computer 14) of the systems and apparatuses disclosed herein may include an interface, logic, and/or memory, any of which may include computer hardware and/or software. An interface can receive input to the component and/or send output from the component, and is typically used to exchange information between, e.g., software, hardware, peripheral devices, users, and combinations of these. A user interface is a type of interface that a user can utilize to communicate with (e.g., send input to and/or receive output from) a computer. Examples of user interfaces include a display, Graphical User Interface (GUI), touchscreen, keyboard, mouse, gesture sensor, microphone, and speakers.

Logic can perform operations of the component. Logic may include one or more electronic devices that process data, e.g., execute instructions to generate output from input. Examples of such an electronic device include a computer, processor, microprocessor (e.g., a Central Processing Unit (CPU)), and computer chip. Logic may include computer software that encodes instructions capable of being executed by an electronic device to perform operations. Examples of computer software include a computer program, application, and operating system.

A memory can store information and may comprise tangible, computer-readable, and/or computer-executable storage medium. Examples of memory include computer memory (e.g., Random Access Memory (RAM) or Read Only Memory (ROM)), mass storage media (e.g., a hard disk), removable storage media (e.g., a Compact Disk (CD) or Digital Video or Versatile Disk (DVD)), database, network storage (e.g., a server), and/or other computer-readable media. Particular embodiments may be directed to memory encoded with computer software.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, or the operations of the systems and apparatuses may be performed by more, fewer, or other components, as apparent to those skilled in the art. As another example, modifications may be made to the methods disclosed herein. The methods may include more, fewer, or other steps, and the steps may be performed in any suitable order, as apparent to those skilled in the art.

To aid the Patent Office and readers in interpreting the claims, Applicants note that they do not intend any of the claims or claim elements to invoke 35 U.S.C. § 112(f), unless the words "means for" or "step for" are explicitly used in the particular claim. Use of any other term (e.g., "mechanism," "module," "device," "unit," "component," "element," "member," "apparatus," "machine," "system," "processor," or "controller") within a claim is understood by the applicants to refer to structures known to those skilled in the relevant art and is not intended to invoke 35 U.S.C. § 112(f).

What is claimed:

1. A system configured to generate image data for an image of an interior of an eye, comprising:
    a camera apparatus comprising:
        a camera stem having a distal end comprising a set of one or more illuminators and an objective lens system, an illuminator configured to emit light, the objective lens system configured to receive light;
        a sensor configured to generate a signal in response to detecting light received by the objective lens system;
        a processor configured to generate the image data from the signal; and a communication interface configured to output the image data; and a patient interface comprising:

a contact portion with an anterior interface surface and a posterior interface surface, the posterior interface surface shaped to conform to an anterior eye surface of the eye; and a sleeve disposed outwardly from the anterior interface surface, the sleeve configured to:

receive the camera stem;

direct light from the set of illuminators towards the interior of the eye; and direct light reflected from the interior of the eye towards the objective lens system of the camera apparatus, the camera apparatus configured to generate the image data for the image of the interior of the eye;

a posterior end of the sleeve having a ball shape; and the anterior interface surface of the contact portion forming a socket shaped to receive the ball-shaped posterior end of the sleeve.

2. The system of claim 1, the contact portion comprising a circular ridge disposed within the socket, the circular ridge circumscribing the opening.

3. The system of claim 1, a central portion of the contact portion forming an opening between the anterior interface surface and the posterior interface surface.

4. The system of claim 1, further comprising a lens disposed within a central portion of the contact portion, the lens configured to:

transmit light from the set of illuminators towards the interior of the eye; and transmit light reflected from the interior of the eye towards the objective lens system of the camera apparatus.

5. The system of claim 4, the lens comprising a wide-angle lens with an angle of view in a range of 64 to 84 degrees.

6. The system of claim 4, the lens comprising an ultra-wide-angle lens with an angle of view in a range of 84 to 180 degrees.

7. The system of claim 1, the contact portion comprising a cuff disposed outwardly from the anterior interface surface, the cuff forming a receptacle configured to receive a depressor for depressing a peripheral retina.

8. The system of claim 1, the camera apparatus further comprising a handle coupled to the camera stem, the handle configured to be held by hand.

9. The system of claim 8:

the handle having a handle axis; and the camera stem having a stem axis, the stem axis at an angle in the range of 0 to 45 degrees relative to the handle axis.

10. The system of claim 8, the handle comprising one or more user controllers, a user controller configured to:

receive a user instruction to perform an action; and provide the instruction to the processor to perform the action.

11. The system of claim 1, the communication interface comprising an interface for a wired communication link.

12. The system of claim 1, the communication interface comprising an interface for a wireless communication link.

13. A method for generating image data for an image of an interior of an eye, comprising:

conforming, by a posterior interface surface of a contact portion of a patient interface, to an anterior eye surface of the eye;

receiving, by a sleeve having a ball shape posterior end of the patient interface, a camera stem of a camera apparatus, the sleeve disposed outwardly from an anterior interface surface of the contact portion forming a socket shaped to receive the ball-shaped posterior end of the sleeve, the camera stem comprising a set of one or more illuminators configured to emit light and an objective lens system configured to receive light;

emitting, by the set of illuminators, light;

directing, by the sleeve, light from the set of illuminators towards the interior of the eye; directing, by the sleeve, light reflected from the interior of the eye towards the objective lens system of the camera apparatus;

generating, by a sensor of the camera apparatus, a signal in response to detecting light received by the objective lens system;

generating, by a processor of the camera apparatus, the image data for the image of the interior of the eye from the signal; and outputting, by a communication interface of the camera apparatus, the image data for the image of the interior of the eye.

14. The method of claim 13, the contact portion comprising a circular ridge disposed within the socket, the circular ridge circumscribing the opening.

15. The method of claim 13, a central portion of the contact portion forming an opening between the anterior interface surface and the posterior interface surface.

16. The method of claim 13, further comprising a lens disposed within a central portion of the contact portion, the method further comprising:

transmitting, by the lens, light from the set of illuminators towards the interior of the eye; and transmitting, by the lens, light reflected from the interior of the eye towards the objective lens system of the camera apparatus.

17. The method of claim 13, the contact portion comprising a cuff disposed outwardly from the anterior interface surface, the cuff forming a receptacle, the method further comprising:

receiving, by the receptable, a depressor for depressing a peripheral retina.

18. The method of claim 13, the camera apparatus further comprising a handle coupled to the camera stem, the handle comprising one or more user controllers, the method further comprising:

receiving, by a user controller, a user instruction to perform an action; and providing the instruction to the processor to perform the action.

* * * * *